(12) United States Patent
Otake

(10) Patent No.: US 10,088,768 B2
(45) Date of Patent: Oct. 2, 2018

(54) YELLOW TONER

(71) Applicant: ZEON CORPORATION, Tokyo (JP)

(72) Inventor: Takuya Otake, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 15/561,590

(22) PCT Filed: Mar. 23, 2016

(86) PCT No.: PCT/JP2016/059268
§ 371 (c)(1),
(2) Date: Sep. 26, 2017

(87) PCT Pub. No.: WO2016/158625
PCT Pub. Date: Oct. 6, 2016

(65) Prior Publication Data
US 2018/0066138 A1 Mar. 8, 2018

(30) Foreign Application Priority Data

Mar. 31, 2015 (JP) .................................. 2015-073264

(51) Int. Cl.
G03G 9/09 (2006.01)
C09B 29/33 (2006.01)
C09B 33/153 (2006.01)
C07C 245/12 (2006.01)

(52) U.S. Cl.
CPC ............. $G03G\ 9/091$ (2013.01); $C09B\ 29/33$ (2013.01); $C09B\ 33/153$ (2013.01); $G03G\ 9/09$ (2013.01); $C07C\ 245/12$ (2013.01)

(58) Field of Classification Search
CPC ...................................................... G03G 9/091
USPC ..................................................... 430/108.23
See application file for complete search history.

(56) References Cited

U.S. PATENT DOCUMENTS

| 2007/0125263 A1 | 6/2007 | Weber et al. |
| 2009/0291377 A1 | 11/2009 | Hirose et al. |
| 2010/0248112 A1* | 9/2010 | Fukushima ........ G03G 9/08755 430/105 |

FOREIGN PATENT DOCUMENTS

| JP | 2005-031163 A | 2/2005 |
| JP | 2006-126384 A | 5/2006 |
| JP | 2006-145625 A | 6/2006 |
| JP | 2007-248746 A | 9/2007 |

OTHER PUBLICATIONS

Notification of Transmittal of Translation of the International Preliminary Report on Patentability (Cahper I) (PCT/IB/338) dated Oct. 12, 2017, issued in PCT/JP2016/059268.

* cited by examiner

Primary Examiner — Janis L Dote
(74) Attorney, Agent, or Firm — Westerman, Hattori, Daniels & Adrian, LLP

(57) ABSTRACT

A yellow toner that is, even in small amounts, better in reflection density and chroma than ever before. Disclosed is a yellow toner containing a binder resin and a yellow colorant, wherein, as the yellow colorant, a compound A represented by the following general formula (1) and a compound B represented by the following formula (2) are contained, and wherein, with respect to 100 parts by mass of the binder resin, a content of the compound A is from 0.5 to 7.5 parts by mass, and a content of the compound B is from 2.5 to 9.0 parts by mass:

General Formula (1)

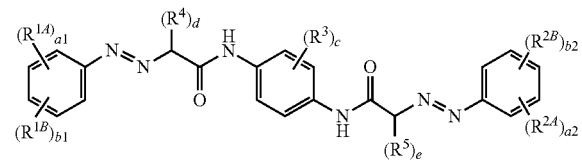

Formula (2)

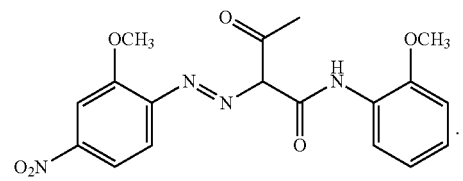

3 Claims, No Drawings

YELLOW TONER

TECHNICAL FIELD

The present invention relates to a yellow toner that is, even in small amounts, better in reflection density and chroma than ever before.

BACKGROUND ART

In an image forming device such as an electrophotographic device and an electrostatic recording device, first, an electrostatic latent image famed on the photoconductor is developed with a toner. Next, as needed, a toner image thus formed is transferred onto a transfer material such as a paper sheet and then fixed thereon by various methods such as heating, pressurization or solvent fume.

In the field of such an image forming device, a digital full-color copying machine and a digital full-color printer have been put to practical use. A digital full-color copying machine produces a full-color image as follows. First, an original color image is subjected to color separation with blue, green and red filters; an electrostatic latent image corresponding to the original color image, which is composed of dots that are 20 to 70 μm in diameter, is developed with yellow, magenta, cyan and black toners; and a full-color image is famed using the subtractive color mixing effect.

Recently, there is an increasing demand for full-color images with high image quality and high resolution. Especially, to increase color reproducibility, it is hoped that an image can be printed in the same hue as ink printing.

As a color pigment for a yellow toner, for example, a disazo pigment as typified by C.I. Pigment Yellow 12, 13 and 17, and a monoazo pigment as typified by C.I. Pigment Yellow 74, 97 and 98 have been generally used.

Patent Literature 1 discloses a yellow toner for developing electrostatic images, the toner comprising a mixed pigment of C.I. Pigment Yellow 74 and C.I. Pigment Yellow 185 as a colorant. In Patent Literature 1, it is described that by mixing C.I. Pigment Yellow 185 with C.I. Pigment Yellow 74, which is a reddish-yellow pigment, the resulting toner has not only the same hue as offset inks, but also low structural viscosity in an organic solvent; therefore, the toner has no difficulty in granulation in water and has better secondary color reproducibility.

Patent Literature 2 discloses a yellow toner comprising C.I. Pigment Yellow 74 and C.I. Solvent Yellow 162. In Patent Literature 2, it is described that by containing these colorants, the toner obtains satisfactory color tone that is obtained in the case of incorporating C.I. Pigment Yellow 74 solely in a toner, and high coloring power of C.I. Solvent Yellow 162.

Patent Literature 3 discloses a yellow toner comprising C.I. Pigment Yellow 74 and C.I. Pigment Yellow 155. In Patent Literature 3, it is described as follows: by allowing C.I. Pigment Yellow 74 and C.I. Pigment Yellow 155 to coexist in a toner material, the pigments inhibit each other's crystal growth even if they are heated during kneading and mixing, and the dispersion of the pigment particles are highly maintained; therefore, a yellow toner that has high coloring power, sharp color tone, satisfactory color mixing property and excellent transparency, is obtained.

Patent Literature 4 discloses a yellow toner comprising C.I. Pigment Yellow 214 and C.I. Pigment Yellow 139 as colorants. Patent Literature 4 describes that a toner excellent in fixability and color properties is obtained by interaction between the amino groups of C.I. Pigment Yellow 214 and the carbonyl groups of C.I. Pigment Yellow 139.

CITATION LIST

Patent Literature 1: Japanese Patent Application Laid-Open (JP-A) No. 2007-248746
Patent Literature 2: JP-A No. 2006-126384
Patent Literature 3: JP-A No. 2005-031163
Patent Literature 4: JP-A No. 2006-145625

SUMMARY OF INVENTION

Technical Problem

The applications of an electrophotographic image forming device have been extended from general copying machines and printers used to print or copy office documents, to the field of production of printed matters for use outside the office, in particular, to the print-on-demand (POD) market that is an area of quick printing, since the image foaming device can easily print variable information from electronic data.

However, due to the following reasons, it cannot be said that the yellow toners disclosed in Patent Literatures 1 to 4 are applicable to the various applications mentioned above. First, the combination of the colorants described in Patent Literature 1 (C.I. Pigment Yellow 74 and C.I. Pigment Yellow 185) is susceptible to humidity and has insufficient environmental stability since C.I. Pigment Yellow 185 is highly hydrophilic. In addition, this combination of the colorants has a problem in that the particle size distribution of the toner deteriorates when the toner is produced by a wet method. The combination of the colorants disclosed in Patent Literature 2 (C.I. Pigment Yellow 74 and C.I. Solvent Yellow 162) has a problem in that C.I. Solvent Yellow 162 has insufficient light resistance and causes a decrease in reflection density over time. For the combination of the colorants disclosed in Patent Literature 3 (C.I. Pigment Yellow 74 and C.I. Pigment Yellow 155), as shown in Comparative Example 3 that will be described below, it is known that when the amount of the toner is smaller than ever before, the smaller amount of the toner is low in reflection density, dark in color, and dull in color. The combination of the colorants disclosed in Patent Literature 4 (C.I. Pigment Yellow 214 and C.I. Pigment Yellow 139) has a problem of low reflection density, since the two pigments have low coloring power. This combination has another problem in that the color is dull since the colorants have a large difference in hue.

For the reflection density and chroma of a printed product, the level of demand has been rapidly increased in recent years, in order to be applicable to the wide range of applications. To meet such a high level of demand, an object of the present invention is to provide a yellow toner that is, even in small amounts, better in reflection density and chroma than ever before.

Solution to Problem

To attain the object, the inventor of the present invention conducted detailed research and found that the yellow toner that shows, even in small amounts, high reflection density and higher chroma than ever before, is obtained by using the combination of compounds A and B as a yellow colorant, each of which has a specific chemical structure. Based on this finding, the inventor achieved the present invention.

The yellow toner of the present invention is a yellow toner comprising a binder resin and a yellow colorant, wherein, as the yellow colorant, a compound A represented by the following general formula (1) and a compound B represented by the following formula (2) are contained, and wherein, with respect to 100 parts by mass of the binder resin, a content of the compound A is from 0.5 to 7.5 parts by mass, and a content of the compound B is from 2.5 to 9.0 parts by mass:

General Formula (1)

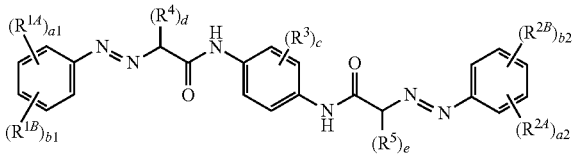

where $R^{1A}$, $R^{1B}$, $R^{2A}$ and $R^{2B}$ are each independently a halogen atom, an alkyl group, a methoxy group, an amino group, a nitro group, an acetylamido group (—$NHCOCH_3$), a methyl ester group (—$COOCH_3$) or a primary amide group (—$CONH_2$);
$R^3$ is a halogen atom;
$R^4$ and $R^5$ are each independently a halogen atom, an alkyl group, a methoxy group, an amino group, a nitro group, an acetylamido group (—$NHCOCH_3$), an acetyl group (—$COCH_3$), a methyl ester group (—$COOCH_3$) or a primary amide group (—$CONH_2$);
a1 and b1 are positive integers that a sum of the positive integers is 1 or more and 3 or less;
a2 and b2 are positive integers that a sum of the positive integers is 1 or more and 3 or less;
c is an integer of 1 or more and 3 or less; and
d and e are each independently 1 or 2, Formula (2)

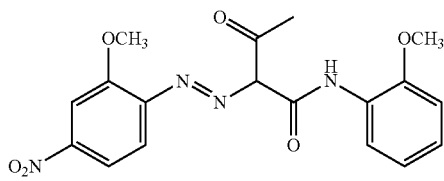

In the present invention, a mass ratio of the content of the compound A to the content of the compound B (compound A/compound B) is preferably from 0.1 to 2.5.

In the present invention, at least any one of the compound A and the compound B is preferably surface-treated with a coupling agent.

Advantageous Effects of Invention

According to the present invention as described above, by using the compound A having the chemical structure represented by the general formula (1) in combination with the compound B, due to the presence of the compound A, the dispersion stability of the compound B in the polymerizable monomer composition or binder resin is increased; therefore, the yellow toner that is, even in small amounts, better in reflection density and chroma than ever before, is provided.

DESCRIPTION OF EMBODIMENTS

The yellow toner of the present invention is a yellow toner comprising a binder resin and a yellow colorant, wherein, as the yellow colorant, a compound A represented by the following general formula (1) and a compound B represented by the following formula (2) are contained, and wherein, with respect to 100 parts by mass of the binder resin, a content of the compound A is from 0.5 to 7.5 parts by mass, and a content of the compound B is from 2.5 to 9.0 parts by mass:

General Formula (1)

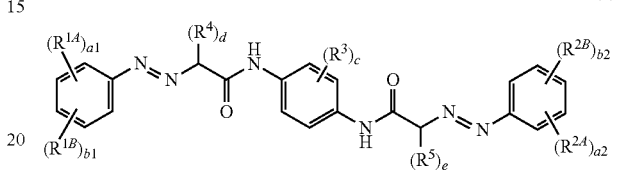

where $R^{1A}$, $R^{1B}$, $R^{2A}$ and $R^{2B}$ are each independently a halogen atom, an alkyl group, a methoxy group, an amino group, a nitro group, an acetylamido group (—$NHCOCH_3$), a methyl ester group (—$COOCH_3$) or a primary amide group (—$CONH_2$); $R^3$ is a halogen atom; $R^4$ and $R^5$ are each independently a halogen atom, an alkyl group, a methoxy group, an amino group, a nitro group, an acetylamido group (—$NHCOCH_3$), an acetyl group (—$COCH_3$), a methyl ester group (—$COOCH_3$) or a primary amide group (—$CONH_2$); a1 and b1 are positive integers that a sum of the positive integers is 1 or more and 3 or less; a2 and b2 are positive integers that a sum of the positive integers is 1 or more and 3 or less; c is an integer of 1 or more and 3 or less; and d and e are each independently 1 or 2, Formula (2)

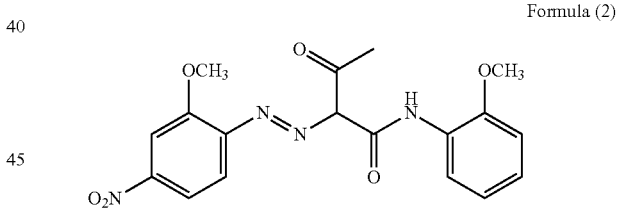

Hereinafter, the yellow toner of the present invention may be simply referred to as "toner".

Hereinafter, a method for producing yellow colored resin particles preferably used in the present invention (hereinafter they may be simply referred to as "colored resin particles"), yellow colored resin particles obtained by the production method, a method for producing a yellow toner using the yellow colored resin particles, and the yellow toner of the present invention will be described in order.

1. Method for Producing Colored Resin Particles

Generally, methods for producing colored resin particles are broadly classified into dry methods such as a pulverization method and wet methods such as an emulsion polymerization agglomeration method, a suspension polymerization method and a solution suspension method. The wet methods are preferred since a toner that has excellent printing characteristics such as image reproducibility can be easily obtained. Among the wet methods, polymerization methods such as the emulsion polymerization agglomeration method and the suspension polymerization method are preferred, since a toner that has relatively small particle size distribution in micron order can be easily obtained. Among the polymerization methods, the suspension polymerization method is more preferred.

The emulsion polymerization agglomeration method is a method for producing colored resin particles by polymerizing emulsified polymerizable monomers to obtain a resin microparticle emulsion, and aggregating the resulting resin microparticles with a colorant dispersion, etc. The solution suspension method is a method for producing colored resin particles by forming droplets of a solution in an aqueous medium, the solution containing toner components such as a binder resin and a colorant dissolved or dispersed in an organic solvent, and removing the organic solvent. Both methods can be carried out by known methods.

The colored resin particles used in the present invention can be produced by the wet methods or the dry methods. The wet methods are preferred, and among the wet methods, the suspension polymerization method is particularly preferred. By the suspension polymerization method, the colored resin particles are produced through the processes described below.

(A) Suspension Polymerization Method
(A-1) Preparation Process of Polymerizable Monomer Composition First, a polymerizable monomer, a yellow colorant, and other additives added as needed, such as a charge control agent and a release agent, are mixed to prepare a polymerizable monomer composition. For example, a media type dispersing machine is used for the mixing in the preparation of the polymerizable monomer composition.

In the present invention, the polymerizable monomer means a monomer having a polymerizable functional group, and the polymerizable monomer is polymerized into a binder resin. As a main component of the polymerizable monomer, a monovinyl monomer is preferably used. As the monovinyl monomer, examples include, but are not limited to, styrene; styrene derivatives such as vinyl toluene and α-methylstyrene; acrylic acid and methacrylic acid; acrylic acid esters such as methyl acrylate, ethyl acrylate, propyl acrylate, butyl acrylate, 2-ethylhexyl acrylate and dimethylaminoethyl acrylate; methacrylic acid esters such as methyl methacrylate, ethyl methacrylate, propyl methacrylate, butyl methacrylate, 2-ethylhexyl methacrylate and dimethylaminoethyl methacrylate; nitrile compounds such as acrylonitrile and methacrylonitrile; amide compounds such as acrylamide and methacrylamide; and olefins such as ethylene, propylene and butylene. These monovinyl monomers may be used alone or in combination of two or more kinds. Among them, styrene, styrene derivatives, and derivatives of acrylic acids or methacrylic acids are preferably used as the monovinyl monomer.

In order to improve hot offset and storage stability, it is preferable to use a crosslinkable polymerizable monomer together with the monovinyl monomer. The crosslinkable polymerizable monomer means a monomer having two or more polymerizable functional groups. As the crosslinkable polymerizable monomer, examples include, but are not limited to, aromatic divinyl compounds such as divinyl benzene, divinyl naphthalene and derivatives thereof; ester compounds such as ethylene glycol dimethacrylate and diethylene glycol dimethacrylate, in which two or more carboxylic acids are esterified to alcohol having two or more hydroxyl groups; other divinyl compounds such as N,N-divinylaniline and divinyl ether; and compounds having three or more vinyl groups. These crosslinkable polymerizable monomers can be used alone or in combination of two or more kinds.

In the present invention, it is desirable that the amount of the crosslinkable polymerizable monomer is generally from 0.1 to 5 parts by mass, and preferably from 0.3 to 2 parts by mass, with respect to 100 parts by mass of the monovinyl monomer.

Also, it is preferable to use a macromonomer as a part of the polymerizable monomer, since the balance between the storage stability and low-temperature fixability of the toner to be obtained can be improved. The macromonomer is a reactive oligomer or polymer having a polymerizable carbon-carbon unsaturated double bond at the end of a polymer chain and generally having a number average molecular mass of from 1,000 to 30,000. The macromonomer is preferably one that can provide a polymer having a higher glass transition temperature (hereinafter may be referred to as "Tg") than a polymer obtained by polymerization of a monovinyl monomer. The amount of the macromonomer is preferably from 0.03 to 5 parts by mass, and more preferably from 0.05 to 1 part by mass, with respect to 100 parts by mass of the monovinyl monomer.

In the present invention, the compound A and the compound B are contained as the yellow colorant.

Hereinafter, the compound A used in the present invention will be described in detail.

The compound A of the present invention is a disazo compound represented by the following general formula (1):

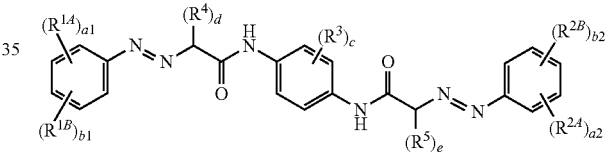

General Formula (1)

In the general formula (1), $R^{1A}$, $R^{1B}$, $R^{2A}$ and $R^{2B}$ are each independently a halogen atom, an alkyl group, a methoxy group, an amino group, a nitro group, an acetylamido group (—NHCOCH$_3$), a methyl ester group (—COOCH$_3$) or a primary amide group (—CONH$_2$). It is preferable that $R^{1A}$, $R^{1B}$, $R^{2A}$ and $R^{2B}$ are each independently a methyl group, a methoxy group, an amino group, a nitro group, an acetylamido group or a primary amide group. It is more preferable that $R^{1A}$ and $R^{2A}$ are methyl groups, and $R^{1B}$ and $R^{2B}$ are primary amide groups. Each of $R^{1A}$, $R^{1B}$, $R^{2A}$, and $R^{2B}$ may have a bond with any carbon atom on the benzene ring (except the carbon atom bound to the azo group (—N═N—)).

In the general formula (1), a1 and b1 are positive integers that a sum of the positive integers is 1 or more and 3 or less, and a2 and b2 are positive integers that a sum of the positive integers is 1 or more and 3 or less. It is preferable that a1, b1, a2 and b2 are each 1.

In the general formula (1), $R^3$ is a halogen atom and is preferably a chlorine atom. $R^3$ may have a bond with any carbon atom on the benzene ring (except the carbon atoms bound to the amide groups (—CO—NH—)).

In the general formula (1), c is an integer of 1 or more and 3 or less, and it is preferably 1.

In the general formula (1), $R^4$ and $R^5$ are each independently a halogen atom, an alkyl group, a methoxy group, an amino group, a nitro group, an acetylamido group (—NHCOCH$_3$), an acetyl group (—COCH$_3$), a methyl ester group (—COOCH$_3$) or a primary amide group (—CONH$_2$). It is preferable that R$^4$ and R$^5$ are acetyl groups.

In the general formula (1), d and e are each independently 1 or 2. It is preferable that d and e are 1.

As the compound A represented by the general formula (1), examples include, but are not limited to, the following compounds. Of the following examples, the compound represented by the following formula (1A) is C.I. Pigment Yellow 214 (CAS No. 254430-12-5) and the compound represented by the following formula (1B) is C.I. Pigment Yellow 219 (CAS No. 347174-87-2).

The compound A used in the present invention is not limited to the following examples. Tautomers of the following examples can be also preferably used as the compound A of the present invention.

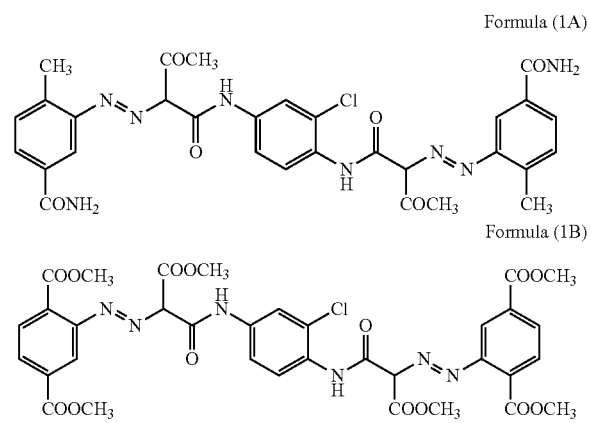

Formula (1A)

Formula (1B)

The compound A may be a commercially-available product or may be synthesized in advance.

As the method for synthesizing the compound A, examples include, but are not limited to, a method of coupling one equivalent of an N,N'-1,4-diacetylphenylenediamine derivative represented by the following general formula (a) with two equivalents of a benzenediazonium derivative represented by the following general formula (b) (see Japanese Examined Patent Application Publication No. 48-13692).

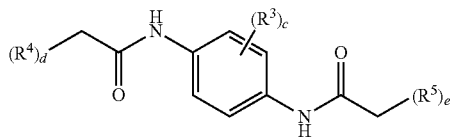

General Formula (a)

where R$^3$, R$^4$ and R$^5$ are the same groups as R$^3$, R$^4$ and R$^5$ in the general formula (1), respectively, and c, d and e are the same numbers as c, d and e in the general formula (1), respectively.

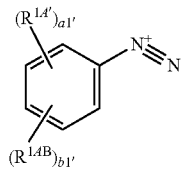

General Formula (b)

where R$^{1A'}$ is the same group as R$^{1A}$ or R$^{2A}$ in the general formula (1); R$^{1B'}$ is the same group as R$^{1B}$ or R$^{2B}$ in the general formula (1); a1' is the same number as a1 or a2 in the general formula (1); and b1' is the same number as b1 or b2 in the general formula (1).

The content of the compound A is from 0.5 to 7.5 parts by mass, preferably from 1.0 to 7.0 parts by mass, more preferably from 2.0 to 6.5 parts by mass, and still more preferably from 3.0 to 6.0 parts by mass, with respect to 100 parts by mass of the binder resin. When the content of the compound A is less than 0.5 part by mass with respect to 100 parts by mass of the binder resin, a target reflection density is not obtained. When the content of the compound A is more than 7.5 parts by mass with respect to 100 parts by mass of the binder resin, the particle size distribution of the toner thus obtained deteriorates.

In the present invention, besides the compound A, the compound B represented by the following formula (2) (C.I. Pigment Yellow 74, CAS No. 6358-31-2) is contained as the yellow colorant.

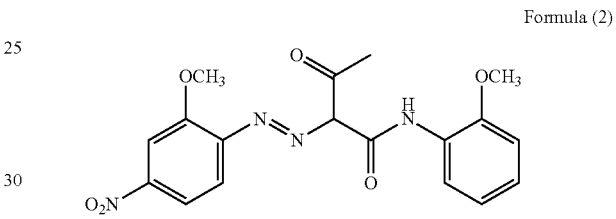

Formula (2)

The content of the compound B is from 2.5 to 9.0 parts by mass, preferably from 3.0 to 7.0 parts by mass, and more preferably from 4.0 to 6.0 parts by mass, with respect to 100 parts by mass of the binder resin. When the content of the compound B is less than 2.5 parts by mass with respect to 100 parts by mass of the binder resin, a target chroma is not obtained. When the content of the compound B is more than 9.0 parts by mass with respect to 100 parts by mass of the binder resin, during the synthesis of the toner, the viscosity of the polymerizable monomer composition increases and makes it difficult to produce the toner.

In the present invention, the mass ratio of the content of the compound A to the content of the compound B (compound A/compound B) is preferably from 0.1 to 2.5.

When the mass ratio is less than 0.1, the yellow toner may be low in reflection density. This is because, as a result of decrease in the content ratio of the compound A, the reflection density increasing effect of the compound A is less likely to be obtained.

When the mass ratio is more than 2.5, the yellow toner may be low in chroma. This is because, as a result of decrease in the content ratio of the compound B, the chroma increasing effect of the compound B is less likely to be obtained.

As just described, since the mass ratio (compound A/compound B) is from 0.1 to 2.5, both the reflection density and chroma of the yellow toner can be increased with balance.

The principle of the effect provided by the use of the combination of the compounds A and B, is not clear. However, it is considered as follows: by using the combination of the compounds, due to the presence of the compound A having the specific chemical structure, the dispersion stability of the compound B in the polymerizable monomer composition or binder resin is increased; therefore, the toner can provide, even in small amounts, a high reflection density and a sharp color.

In the present invention, the yellow toner preferably contains the yellow colorant surface-treated with a coupling agent.

As the coupling agent, examples include, but art not limited to, a silane coupling agent, a titanium coupling agent, and an aluminum coupling agent. Of them, an aluminum coupling agent is preferred. The amount of the coupling agent added is preferably from 0.05 to 5 parts by mass, more preferably from 0.2 to 4 parts by mass, and still more preferably from 1 to 3 parts by mass, with respect to 100 parts by mass of the yellow colorant. When the amount of the coupling agent is more than 5 parts by mass, a coagulum may be produced. When the amount of the coupling agent is less than 0.05 part by mass, both the reflection density and chroma of the thus-obtained toner may not be increased.

The aluminum coupling agent is preferably used in the present invention. Hereinafter, the aluminum coupling agent will be described. As the aluminum coupling agent, examples include, but are not limited to, alkyl acetoacetate aluminum diisopropylate, aluminum tris(ethyl acetoacetate), aluminummonoacetylacetate bis(alkyl acetoacetate) and aluminum tris(acetylacetate).

Of these aluminum coupling agents, alkyl acetoacetate aluminum diisopropylate represented by the following general formula (i) is preferred:

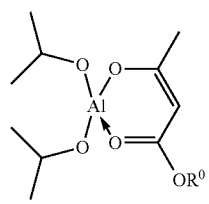

General Formula (i)

where $R^0$ is an alkyl group.

$R^0$ is generally an alkyl group having 10 to 30 carbon atoms, and preferably an alkyl group having 15 to 25 carbon atoms. The aluminum coupling agent is particularly preferably a compound represented by the general formula (i) where R=18.

The aluminum coupling agent may be one that imparts a nitrogen-containing functional group to the surface of the yellow colorant by a coupling reaction. In this case, as the nitrogen-containing functional group of the aluminum coupling agent, examples include, but are not limited to, a primary amino group, a secondary amino group, a tertiary amino group, and a group having a ketimine structure represented by the following general formula (3):

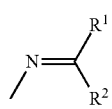

General Formula (3)

where $R^1$ and $R^2$ are each a hydrogen atom or an alkyl group.

Among nitrogen-containing aluminum coupling agents, preferred is one that functions finally as an aluminum-containing amino coupling agent (that is, an aluminum coupling agent that imparts an amino group to the surface of the yellow colorant by a coupling reaction). Since the coupling agent is needed to finally function as an aluminum-containing amino coupling agent, it may be an aluminum-containing amino coupling agent in which the amino group is derivatized at the time of a coupling reaction and which has a switching function that can regain the amino group when needed. As such an aluminum-containing amino coupling agent, examples include, but are not limited to, an aluminum-containing amino coupling agent having a ketimine structure.

A typical aluminum coupling agent that is preferably used in the present invention, is represented by the following general formula (4):

$R_mAlY_n$      General Formula (4):

where R is an alkoxy group or a chlorine atom; Y is an amino group or an amino derivative group that can regain an amino group; Y is preferably a primary amino group or an amino derivative group that can regain a primary amino group; m is 1 or 2; n is 1 or 2; m+n=3; a plurality of R's represented by the same sign may be the same or different from each other; and a plurality of Y's represented by the same sign may be the same or different from each other.

As the aluminum-containing amino coupling agent represented by the general formula (4) include, but are not limited to, compounds represented by the following structural formulae. All or part of alkoxy groups in each of the following structural formulae may be replaced by chlorine atoms. The aluminum-containing amino coupling agents may be used in combination of two or more kinds.

| | |
|---|---|
| $H_2NCH_2CH_2CH_2Al(OCH_3)_2$ | Compound (1): |
| $H_2NCH_2CH_2CH_2Al(OC_2H_5)_2$ | Compound (2): |
| $H_2NCH_2CH_2CH_2Al(CH_3)(OCH_3)$ | Compound (3): |
| $H_2NCH_2CH_2NHCH_2CH_2CH_2Al(CH_3)(OCH_3)$ | Compound (4): |
| $H_2NCONHCH_2CH_2CH_2Al(OC_2H_5)_2$ | Compound (5): |
| $H_2NCH_2CH_2NHCH_2CH_2CH_2Al(OCH_3)_2$ | Compound (6): |
| $H_2NCH_2CH_2NHCH_2CH_2NHCH_2CH_2CH_2Al(OCH_3)_2$ | Compound (7): |
| $H_5C_2OCOCH_2CH_2NHCH_2CH_2CH_2Al(OCH_3)_2$ | Compound (8): |
| $H_5C_2OCOCH_2CH_2NHCH_2CH_2NHCH_2CH_2CH_2Al(OCH_3)_2$ | Compound (9): |
| $H_5C_2OCOCH_2CH_2NHCH_2CH_2NHCH_2CH_2NHCH_2CH_2NHCH_2CH_2CH_2Al(OCH_3)_2$ | Compound (10): |
| $H_3COCOCH_2CH_2NHCH_2CH_2NHCH_2CH_2CH_2Al(OCH_3)_2$ | Compound (11): |
| $(H_5C_2)_2NCH_2CH_2CH_2Al(OC_2H_5)_2$ | Compound (12): |

Compound (13)

$H_2N$—⟨benzene⟩—$Al(OCH_3)_3$

Compound (14)

⟨benzene⟩—$NHCH_2CH_2CH_2Al(OCH_3)_2$

Compound (15)

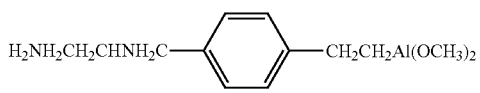

Especially from the viewpoint of the dispersibility of the yellow colorant and the environmental stability of the thus-obtained toner, an aluminum coupling agent that finally imparts a primary amino group, is preferred. As the aluminum coupling agent that finally imparts a primary amino group, examples include, but are not limited to, a typical aluminum-containing primary amino coupling agent that has a primary amino group from the beginning, and an aluminum coupling agent in which the primary amino group part is derivatized and which has a switching function, such as a nitrogen-containing aluminum coupling agent having a ketimine structure (the following compound (16)). An aluminum coupling agent having a ketimine structure is particularly preferred.

Chemical Formula (16)

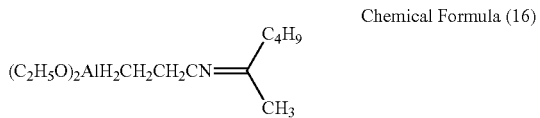

The method for surface-treating the yellow colorant with the nitrogen-containing aluminum coupling agent may be a wet treatment method or a dry treatment method.

The wet treatment method is carried out as follows: a solution of the nitrogen-containing aluminum coupling agent is prepared; the yellow colorant is added therein to be famed into a slurry; the slurry thus obtained is sufficiently stirred and mixed; the yellow colorant is separated therefrom by decantation, centrifugal separation or the like; the separated yellow colorant is dried by heating and, as needed, pulverized again, thereby completing the surface treatment. By the wet treatment method, the surface can be easily and uniformly treated.

In general, the nitrogen-containing aluminum coupling agent is used for the surface treatment in the form of an aqueous solution in which the content of the nitrogen-containing aluminum coupling agent is from about 0.1 to 2.0% by mass. When the nitrogen-containing aluminum coupling agent has poor compatibility with water, a component for increasing the solubility of the coupling agent may be added, such as an acetic acid aqueous solution of from about 0.1 to 2.0% by mass, a mixed solution of water and alcohol, or a mixed solution of acetic acid aqueous solution and alcohol. In the case of the typical aluminum-containing primary amino coupling agent that has a primary amino group from the beginning, a diluted solution of the coupling agent can be prepared with water or a solution having a low acetic acid concentration. In the case of an aluminum-containing primary amino coupling agent that has a primary amino group derivatized into a ketimine or the like, the coupling agent may not be sufficiently dissolved only with water. In this case, it is preferable to prepare an aqueous solution of the coupling agent with an acetic acid aqueous solution of from about 0.1 to 2.0% by mass. Acetic acid has an effect of accelerating the hydrolysis of an aluminum coupling agent and an effect of controlling the pH of the aqueous solution within a weakly acidic range that increases the stability of silanol.

The process of preparing the aqueous solution of the nitrogen-containing aluminum coupling agent is as follows. First, while stirring water, or while stirring water that contains other component such as an acetic acid aqueous solution as needed, the aluminum coupling agent is added dropwise thereto. The stirring rate should be as fast as possible, while preventing the solution from splashing. To prevent gelation of the solution, the rate of dropwise addition should not be fast. Even after the dropwise addition is completed, the stirring is further continued for 30 to 60 minutes. The hydrolysis of the aluminum coupling agent ends when the aqueous solution becomes almost clear. As needed, the aqueous solution is filtered and used. When an insoluble or suspended matter is apparent, the aqueous solution is subjected to cycle filtration with a cartridge having a pore diameter of 0.5 μm or less.

Meanwhile, in the case of the dry treatment method, it is carried out as follows. First, a capacitively small amount of diluted or undiluted solution of the nitrogen-containing aluminum coupling agent is added to the yellow colorant. They are sufficiently stirred, mixed and dried to complete the surface treatment, while preventing the yellow colorant from being slurried and while keeping the colorant in a powdery state. After the stirring, as needed, the mixture may be matured to apply the coupling agent to the yellow colorant and then dried. A stirrer is used for the stirring. As the stirrer, examples include, but are not limited to, FM Mixer (product name) and a V-type blender. By the wet treatment method, the process of separating the yellow colorant from an excess treatment solution is not needed, and energy required for drying moisture can be saved. Therefore, the wet treatment method can reduce the treatment cost and is suitable for mass processing.

In the case of the dry treatment method, it is carried out as follows, for example. First, while stirring the yellow colorant with FM Mixer (product name), 10 to 100 parts by mass of a treatment solution having a nitrogen-containing aluminum coupling agent concentration of from 0.1 to 10% by mass, is added to 100 parts by mass of the yellow colorant. They are stirred for about 10 minutes to sufficiently apply the treatment solution to the yellow colorant. The treatment solution is further added to the yellow colorant so that the total amount of the treatment solution is from 1 to 10 parts. The mixture is heated at a temperature of from 80 to 100° C. for about one hour, thereby completing the surface treatment of the yellow colorant.

As another additive, a positively or negatively chargeable charge control agent can be used to improve the chargeability of the toner.

The charge control agent is not particularly limited, as long as it is one that is generally used as a charge control agent for toners. Among charge control agents, a positively or negatively chargeable charge control resin is preferred, since the charge control resin is highly compatible with the polymerizable monomer and can impart stable chargeability (charge stability) to the toner particles. From the viewpoint of obtaining a positively chargeable toner, a positively chargeable charge control resin is more preferred.

As the positively chargeable charge control agent, examples include, but are not limited to, a nigrosine dye, a quaternary ammonium salt, a triaminotriphenylmethane compound, an imidazole compound, a polyamine resin, a quaternary ammonium group-containing copolymer, and a quaternary ammonium salt group-containing copolymer, which are preferably used as the charge control resin.

As the negatively chargeable charge control agent, examples include, but are not limited to, an azo dye containing a metal such as Cr, Co, Al and Fe; a metal salicylate compound; a metal alkylsalicylate compound; and a sulfonic acid group-containing copolymer, a sulfonic acid salt group-containing copolymer, a carboxylic acid group-containing copolymer and a carboxylic acid salt group-containing copolymer, which are preferably used as the charge control resin.

In the present invention, it is desirable that the amount of the charge control agent is generally from 0.01 to 10 parts by mass, and preferably from 0.03 to 8 parts by mass, with respect to 100 parts by mass of the monovinyl monomer. When the added amount of the charge control agent is less than 0.01 part by mass, fog may occur. On the other hand, when the added amount of the charge control agent is more than 10 parts by mass, soiling in printing may occur.

As another additive, a molecular weight modifier is preferably used in the polymerization of the polymerizable monomer that is polymerized into a binder resin.

The molecular weight modifier is not particularly limited, as long as it is one that is generally used as a molecular weight modifier for toners. As the molecular weight modifier, examples include, but are not limited to, mercaptans such as t-dodecyl mercaptan, n-dodecyl mercaptan, n-octyl mercaptan and 2,2,4,6,6-pentamethylheptane-4-thiol, and thiuram disulfides such as tetramethyl thiuram disulfide, tetraethyl thiuram disulfide, tetrabutyl thiuram disulfide, N,N'-dimethyl-N,N'-diphenyl thiuram disulfide, and N,N'-dioctadecyl-N,N'-diisopropyl thiuram disulfide. These molecular weight modifiers may be used alone or in combination of two or more kinds.

In the present invention, it is desirable that the amount of the molecular weight modifier is generally from 0.01 to 10 parts by mass, and preferably 0.1 to 5 parts by mass, with respect to 100 parts by mass of the monovinyl monomer.

As another additive, it is preferable to add a release agent. By adding the release agent, the releasability of the toner from a fixing roller upon fixing, can be improved. The release agent is not particularly limited, as long as it is one that is generally used as a release agent in toner. As the release agent, examples include, but are not limited to, low-molecular-weight polyolefin waxes and modified waxes thereof; natural plant waxes such as jojoba; petroleum waxes such as paraffin; mineral waxes such as ozokerite; synthetic waxes such as Fischer-Tropsch wax; and polyalcohol esters such as dipentaerythritol ester. Of them, polyalcohol esters are preferred since the toner can achieve a balance between storage stability and low-temperature fixability. These release agents may be used alone or in combination of two or more kinds.

The amount of the release agent is preferably from 0.1 to 30 parts by mass, and more preferably from 1 to 20 parts by mass, with respect to 100 parts by mass of the monovinyl monomer.

(A-2) Suspension Process of obtaining Suspension (Droplets Forming Process)

In the present invention, the polymerizable monomer composition containing the polymerizable monomer and the yellow colorant is dispersed in an aqueous medium containing a dispersion stabilizer, and a polymerization initiator is added therein. Then, the polymerizable monomer composition are famed into droplets. The method for foaming the droplets is not particularly limited. For example, the droplets are famed by means of a device capable of strong stirring, such as an (in-line type) emulsifying and dispersing machine (product name: Milder, manufactured by: Pacific Machinery & Engineering Co., Ltd.) and a high-speed emulsifying and dispersing machine (product name: T. K. Homomixer Mark II, manufactured by: PRIMIX Corporation).

As the polymerization initiator, examples include, but are not limited to, persulfates such as potassium persulfate and ammonium persulfate; azo compounds such as 4,4'-azobis (4-cyanovaleric acid), 2,2'-azobis(2-methyl-N-(2-hydroxyethyl)propionamide), 2,2'-azobis(2-amidinopropane)dihydrochloride, 2,2'-azobis(2,4-dimethylvaleronitrile) and 2,2'-azobisisobutyronitrile; and organic peroxides such as di-t-butylperoxide, benzoylperoxide, t-butylperoxy-2-ethylhexanoate, t-hexylperoxy-2-ethylbutanoate, diisopropylperoxydicarbonate, di-t-butylperoxyoxyisophthalate and t-butylperoxyisobutyrate. They can be used alone or in combination of two or more kinds. Among them, organic peroxides are preferred since they can reduce residual polymerizable monomer and impart excellent printing durability.

Among organic peroxides, preferred are peroxy esters, and more preferred are non-aromatic peroxy esters, i.e., peroxy esters having no aromatic ring, since they have excellent initiator efficiency and can reduce residual polymerizable monomer.

The polymerization initiator may be added after the polymerizable monomer composition is dispersed into the aqueous medium and before the polymerizable monomer composition is famed into droplets as described above, or it may be added to the polymerizable monomer composition before the polymerizable monomer composition is dispersed into the aqueous medium.

The added amount of the polymerization initiator used for the polymerization of the polymerizable monomer composition, is preferably from 0.1 to 20 parts by mass, more preferably from 0.3 to 15 parts by mass, and even more preferably from 1 to 10 parts by mass, with respect to 100 parts by mass of the monovinyl monomer.

In the present invention, the aqueous medium means a medium containing water as a main component.

In the present invention, the dispersion stabilizer is preferably added to the aqueous medium. As the dispersion stabilizer, examples include, but are not limited to, inorganic compounds including sulfates such as barium sulfate and calcium sulfate, carbonates such as barium carbonate, calcium carbonate and magnesium carbonate, phosphates such as calcium phosphate, metal oxides such as aluminum oxide and titanium oxide, and metal hydroxides such as aluminum hydroxide, magnesium hydroxide and iron(II) hydroxide, and organic compounds including water-soluble polymers such as polyvinyl alcohol, methyl cellulose and gelatin, anionic surfactants, nonionic surfactants, and ampholytic surfactants. These dispersion stabilizers can be used alone or in combination of two or more kinds.

Among the above dispersion stabilizers, preferred are colloids of inorganic compounds, and particularly preferred is a colloid of a hardly water-soluble metal hydroxide. By using a colloid of an inorganic compound, particularly a colloid of a hardly water-soluble metal hydroxide, the colored resin particles can have a narrow particle size distribution, and the amount of the dispersion stabilizer remaining after washing can be small, so that the polymerization toner thus obtained can clearly reproduce an image and does not deteriorate environmental stability.

(A-3) Polymerization Process

Formation of the droplets is carried out as described under the above (A-2). The thus-obtained aqueous dispersion medium is heated to polymerize, thereby foaming an aqueous dispersion containing the yellow colorant.

The polymerization temperature of the polymerizable monomer composition is preferably 50° C. or more, and more preferably from 60 to 95° C. The polymerization reaction time is preferably from 1 to 20 hours, and more preferably from 2 to 15 hours.

The colored resin particles may be used as they are as a polymerization toner, or they may be mixed with an external additive and used as a polymerization toner. It is preferable that the colored resin particles are so-called core-shell type (or "capsule type") colored resin particles obtained by using the colored resin particles as a core layer and foaming a shell layer, which is a layer that is different from the core layer, around the core layer. By covering the core layer composed of a substance having a low softening point with a substance having a higher softening point, the core-shell type colored resin particles can achieve a balance between lowering of fixing temperature and prevention of aggregation during storage.

A method for producing the above-mentioned core-shell type colored resin particles using the colored resin particles, is not particularly limited. The core-shell type colored resin particles can be produced by a conventional method. The in situ polymerization method and the phase separation method are preferable from the viewpoint of production efficiency.

Hereinafter, the method for producing the core-shell type colored resin particles by the in situ polymerization method, will be described.

The core-shell type colored resin particles can be obtained by adding a polymerizable monomer for foaming a shell layer (a polymerizable monomer for shell) and a polymerization initiator to an aqueous medium in which the colored resin particles are dispersed, and then polymerizing the mixture.

As the polymerizable monomer for shell, the above-mentioned polymerizable monomers can be used. Among the polymerizable monomers, it is preferable to use monomers that can provide a polymer having a Tg of more than 80° C., such as styrene, acrylonitrile and methyl methacrylate, alone or in combination of two or more kinds.

As the polymerization initiator used for polymerization of the polymerizable monomer for shell, examples include, but are not limited to, water-soluble polymerization initiators including metal persulfates such as potassium persulfate and ammonium persulfate, and azo-type initiators such as 2,2'-azobis(2-methyl-N-(2-hydroxyethyl)propionamide) and 2,2'-azobis(2-methyl-N-(1,1-bis(hydroxymethyl)2-hydroxyethyl)propionamide). These polymerization initiators can be used alone or in combination of two or more kinds. The amount of the polymerization initiator is preferably from 0.1 to 30 parts by mass, and more preferably from 1 to 20 parts by mass, with respect to 100 parts by mass of the polymerizable monomer for shell.

The polymerization temperature of the shell layer is preferably 50° C. or more, and more preferably from 60 to 95° C. The polymerization reaction time is preferably from 1 to 20 hours, and more preferably from 2 to 15 hours.

(A-4) Washing, Filtering, Dehydrating and Drying Processes

After the polymerization is completed, the aqueous dispersion of the colored resin particles obtained by the polymerization is preferably subjected to operations of filtering, washing for removal of the dispersion stabilizer, dehydrating and drying, several times as needed, according to a conventional method.

The washing is preferably carried out by the following method. When the inorganic compound is used as the dispersion stabilizer, acid or alkali is added to the aqueous dispersion of the colored resin particles, thereby dissolving the dispersion stabilizer in water and removing it. When the colloid of the hardly water-soluble inorganic hydroxide is used as the dispersion stabilizer, the pH of the aqueous dispersion of the colored resin particles is controlled to 6.5 or less by adding acid. As the acid, examples include, but are not limited to, inorganic acids such as sulfuric acid, hydrochloric acid and nitric acid, and organic acids such as formic acid and acetic acid. Sulfuric acid is particularly preferred for its high removal efficiency and small impact on production facilities.

The dehydrating and filtering method is not particularly limited and can be selected from various known methods. As the method, examples include, but are not limited to, a centrifugal filtration method, a vacuum filtration method and a pressure filtration method. Also, the drying method is not particularly limited and can be selected from various methods.

(B) Pulverization Method

In the case of producing the colored resin particles by employing the pulverization method, the colored resin particles are produced by the following processes.

First, a binder resin, a yellow colorant, and other additives added as needed, such as a charge control agent and a release agent, are mixed by means of a mixer such as a ball mill, a V-type mixer, FM Mixer (product name), a high-speed dissolver, an internal mixer or Forberg.

Next, while heating the thus-obtained mixture, the mixture is kneaded by means of a press kneader, a twin screw kneading machine, a roller or the like. The thus-obtained kneaded product is coarsely pulverized by means of a pulverizer such as a hammer mill, a cutter mill or a roller mill, finely pulverized by means of a pulverizer such as a jet mill or a high-speed rotary pulverizer, and then classified into a desired particle diameter by means of a classifier such as a wind classifier or an airflow classifier, thereby obtaining the colored resin particles produced by the pulverization method.

In the pulverization method, those that are provided above under "(A) Suspension polymerization method" can be used as the binder resin, the yellow colorant, and the other additives added as needed, such as the charge control agent and the release agent. Similarly to the colored resin particles obtained by the above "(A) Suspension polymerization method", the colored resin particles obtained by the pulverization method can be core-shell type colored resin particles by a method such as the in situ polymerization method.

As the binder resin, resins that have been widely used for toners can be used. As the binder resin used in the pulverization method, examples include, but are not limited to, polystyrene, styrene-butyl acrylate copolymers, polyester resins and epoxy resins.

2. Colored Resin Particles

The colored resin particles containing the yellow colorant are obtained by the production method such as the above-mentioned "(A) Suspension polymerization method" or "(B) Pulverization method".

Hereinafter, the colored resin particles constituting the toner will be described. The colored resin particles described below encompass both core-shell type colored resin particles and colored resin particles of other types.

The volume average particle diameter (Dv) of the colored resin particles is preferably from 3 to 15 µm, and more preferably from 4 to 12 µm. When the volume average particle diameter (Dv) is less than 3 µm, the flowability of the polymerization toner decreases and may deteriorate transferability or decrease image density. When the volume average particle diameter (Dv) is more than 15 μm, image resolution may decrease.

For the colored resin particles, the ratio (Dv/Dn) of the volume average particle diameter (Dv) and the number average particle diameter (Dn) is preferably from 1.0 to 1.3, and more preferably from 1.0 to 1.2. When the ratio Dv/Dn is more than 1.3, there may be a decrease in transferability, image density and resolution. The volume average particle diameter and number average particle diameter of the colored resin particles can be measured by means of a particle size analyzer (product name: Multisizer, manufactured by: Beckman Coulter, Inc.), for example.

The average circularity of the colored resin particles of the present invention is preferably from 0.96 to 1.00, more preferably from 0.97 to 1.00, and even more preferably from 0.98 to 1.00, from the viewpoint of image reproducibility.

When the average circularity of the colored resin particles is less than 0.96, thin line reproducibility in printing may deteriorate.

As the toner of the present invention, the colored resin particles containing the yellow colorant can be used as they are. From the viewpoint of controlling the chargeability, flowability and storage stability of the toner, the colored resin particles may be used as a one-component toner by mixing and stirring the colored resin particles with the external additives to attach the external additives to the surface of the colored resin particles.

The one-component toner may be mixed and stirred with carrier particles to obtain a two-component developer.

A stirrer is used to cover the colored resin particles with the external additives. The stirrer is not particularly limited, as long as it is a stirring device that can attach the external additives to the surface of the colored resin particles. For example, the colored resin particles can be covered with the external additives by means of a stirrer that is capable of mixing and stirring, such as FM Mixer (product name, manufactured by: Nippon Coke & Engineering Co., Ltd.), Super Mixer (product name, manufactured by: Kawata Manufacturing Co., Ltd.), Q Mixer (product name, manufactured by: Nippon Coke & Engineering Co., Ltd.), Mechanofusion System (product name, manufactured by: Hosokawa Micron Corporation) and Mechanomill (product name, manufactured by: Okada Seiko Co., Ltd.)

As the external additives, examples include, but are not limited to, inorganic fine particles composed of silica, titanium oxide, aluminum oxide, zinc oxide, tin oxide, calcium carbonate, calcium phosphate and/or cerium oxide, and organic fine particles composed of polymethyl methacrylate resin, silicone resin and/or melamine resin. Of them, inorganic fine particles are preferred. Of inorganic fine particles, silica and/or titanium oxide is preferred, and fine particles composed of silica are particularly preferred.

These external additives can be used alone. However, it is preferable to use them in combination of two or more kinds.

In the present invention, it is desirable that the external additives are used in an amount of generally from 0.05 to 6 parts by mass, preferably from 0.2 to 5 parts by mass, with respect to 100 parts by mass of the colored resin particles. When the added amount of the external additives is less than 0.05 part by mass, toner transferability may decrease. When the added amount of the external additives is more than 6 parts by mass, fog may occur.

4. Toner of the Present Invention

The toner of the present invention obtained through the above steps uses the combination of the compound A and the compound B as the yellow colorant; therefore, the toner of the present invention is a yellow toner that is, even in small amounts, better in reflection density and chroma than ever before.

EXAMPLES

Hereinafter, the present invention will be described further in detail, with reference to examples and comparative examples. However, the scope of the present invention may not be limited to the following examples. Herein, "part(s)" and "%" are based on mass if not particularly mentioned.

Test methods used in the examples and the comparative examples are as follows.
1. Production of Colored Resin Particles
<Colored Resin Particles (1)>
1-1. Preparation of Polymerizable Monomer Composition for Core The following raw materials were subjected to wet pulverization by means of a media-type disperser: 75 parts of styrene, 25 parts of n-butyl acrylate, 0.1 part of a polymethacrylic acid ester macromonomer (product name: AA6, manufactured by: TOAGOSEI Co., Ltd., Tg: 94° C.), 0.7 part of divinylbenzene, 1.0 part of tetraethylthiuram disulfide, 0.2 part of an aluminum coupling agent (product name: Plenact AL-M, manufactured by: Ajinomoto Fine-Techno. Co., Inc.) and, as yellow pigment, 3.0 parts of C.I. Pigment Yellow 214 (represented by the following formula (1A), product name: PV Fast Yellow H9G VP2430, manufactured by: Clariant Corp., CAS No. 254430-12-5) and 5.0 parts of C.I. Pigment Yellow 74 (product name: Fast Yellow 7413, manufactured by: Sanyo Color Works, Ltd.) To a mixture obtained by the wet pulverization, 0.75 part of a charge control resin (product name: Acrybase FCA-161P, manufactured by: Fujikura Kasei Co., Ltd.) and 10 parts of an ester wax (product name: WEPT, manufactured by: NOF Corporation) were added, mixed and dissolved to obtain a polymerizable monomer composition.

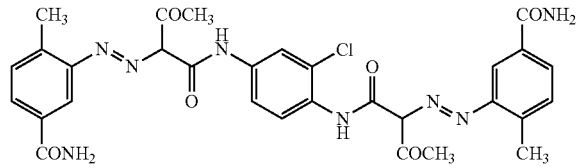

Formula (1A)

1-2. Preparation of Aqueous Dispersion Medium

An aqueous solution of 7.3 parts of sodium hydroxide dissolved in 50 parts of ion-exchanged water, was gradually added to an aqueous solution of 10.4 parts of magnesium chloride dissolved in 280 parts of ion-exchanged water, while stirring, thereby preparing a magnesium hydroxide colloid dispersion.

1-3. Preparation of Polymerizable Monomer for Shell

Meanwhile, 2 parts of methyl methacrylate and 130 parts of water were subjected to a fine dispersion treatment by means of an ultrasonic emulsifying machine, thereby preparing an aqueous dispersion of a polymerizable monomer for shell.

1-4. Droplets Forming Process

The polymerizable monomer composition was put in the magnesium hydroxide colloid dispersion (the magnesium hydroxide colloid amount: 5.3 parts) and stirred. Then, as a polymerization initiator, 6 parts of t-butylperoxy-2-ethylhexanoate was added thereto. The dispersion containing the polymerization initiator was subjected to dispersion at 15,000 rpm using an in-line type emulsifying and dispersing machine (product name: Milder, manufactured by: Pacific Machinery & Engineering Co., Ltd.), thereby forming the polymerizable monomer composition into droplets.

1-5. Suspension Polymerization Process

The dispersion containing the droplets of the polymerizable monomer composition was put in a reactor. The temperature thereof was increased to 90° C. to start a polymerization reaction. After the polymerization conversion rate reached almost 100%, a solution obtained by dissolving 0.1 part of 2,2'-azobis[2-methyl-N-(2-hydroxyethyl)-propionamide] (a water-soluble polymerization initiator, product name: VA-086, manufactured by: Wako Pure Chemical Industries, Ltd.) in the aqueous dispersion for the polymerizable monomer for shell, was added in the reactor. Next, the temperature of the reactor was kept at 95° C. for 4 hours to continue the polymerization further. Then, the reactor was cooled by water to stop the reaction, thereby obtaining an aqueous dispersion of core-shell type colored resin particles.

1-6. Post-Treatment Process

The aqueous dispersion of the colored resin particles was subjected to acid washing (25° C., 10 minutes) in which, while stirring the aqueous dispersion, sulfuric acid was added thereto until the pH of the aqueous dispersion was 4.5 or less. Then, the colored resin particles were separated from the aqueous dispersion by filtration and washed with water. The washing water was filtered. A filtrate thus obtained had an electrical conductivity of 20 μS/cm. The colored resin particles subjected to the washing and filtering processes were dehydrated and dried to obtain dried colored resin particles (1).

<Colored Resin Particles (2)>

Colored resin particles (2) were obtained in the same manner as the production method of the colored resin particles (1), except that in the "Preparation of polymerizable monomer composition for core", the added amount of C.I. Pigment Yellow 214 was changed from 3.0 parts to 4.0 parts.

<Colored Resin Particles (3)>

Colored resin particles (3) were obtained in the same manner as the production method of the colored resin particles (1), except that in the "Preparation of polymerizable monomer composition for core", the added amount of C.I. Pigment Yellow 214 was changed from 3.0 parts to 6.0 parts, and the added amount of C.I. Pigment Yellow 74 was changed from 5.0 parts to 4.0 parts.

<Colored Resin Particles (4)>

Colored resin particles (4) were obtained in the same manner as the production method of the colored resin particles (1), except that in the "Preparation of polymerizable monomer composition for core", 3.0 parts of C.I. Pigment Yellow 214 was changed to 3.0 parts of C.I. Pigment Yellow 93 (represented by the following formula (X), product name: Cromophtal Yellow 3G, manufactured by: BASF, CAS No. 5580-57-4).

Formula (X)

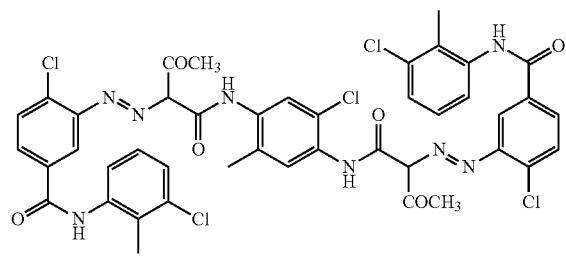

<Colored Resin Particles (5)>

Colored resin particles (5) were obtained in the same manner as the production method of the colored resin particles (1), except that in the "Preparation of polymerizable monomer composition for core", 3.0 parts of C.I. Pigment Yellow 214 was changed to 3.0 parts of C.I. Pigment Yellow 138 (represented by the following formula (Y), product name: Paliotol Yellow K0961 HD, manufactured by: BASF, CAS No. 30125-47-4).

Formula (Y)

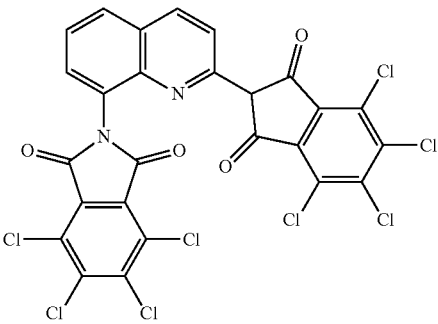

<Colored Resin Particles (6)>

Colored resin particles (6) were obtained in the same manner as the production method of the colored resin particles (1), except that in the "Preparation of polymerizable monomer composition for core", 3.0 parts of C.I. Pigment Yellow 214 was changed to 3.0 parts of C.I. Pigment Yellow 155 (represented by the following formula (Z), product name: Toner Yellow 3GP, manufactured by: Clariant Corp., CAS No. 68516-73-4).

Formula (Z)

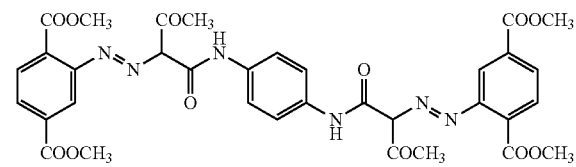

<Colored Resin Particles (7)>

Colored resin particles (7) were obtained in the same manner as the production method of the colored resin particles (1), except that in the "Preparation of polymerizable monomer composition for core", the added amount of C.I. Pigment Yellow 214 was changed from 3.0 parts to 8.0 parts, and 5.0 parts of C.I. Pigment Yellow 74 was not used.

<Colored Resin Particles (8)>

Colored resin particles (8) were obtained in the same manner as production method of the colored resin particles (1), except that in the "Preparation of polymerizable monomer composition for core", the added amount of C.I. Pigment Yellow 214 was changed from 3.0 parts to 10.0 parts, and the added amount of C.I. Pigment Yellow 74 was changed from 5.0 parts to 2.0 parts.

<Colored Resin Particles (9)>

Colored resin particles (9) were obtained in the same manner as the production method of the colored resin particles (1), except that in the "Preparation of polymerizable monomer composition for core", 3.0 parts of C.I. Pigment Yellow 214 was not used, and the added amount of C.I. Pigment Yellow 74 was changed from 5.0 parts to 8.0 parts.

2. Evaluation of Properties of Colored Resin Particles

Measurement of volume average particle diameter (Dv) and calculation of particle size distribution (Dv/Dn) were carried out on the colored resin particles (1) to (9).

About 0.1 g of a measurement sample (colored resin particles) was weighed out and put in a beaker. As a dispersant, 0.1 mL of an alkylbenzene sulfonic acid aqueous solution (product name: Driwel, manufactured by: Fujifilm Corporation) was added thereto. In addition, 10 to 30 mL of Isoton II was added to the beaker. The mixture was dispersed for three minutes with a 20W ultrasonic disperser. Then, the volume average particle diameter (Dv) and number average particle diameter (Dn) of the colored resin particles were measured with a particle diameter measuring device (product name: Multisizer, manufactured by: Beckman Coulter, Inc.) in the following conditions:

Aperture diameter: 100 μm
Medium: Isoton II
Number of measured particles: 100,000

Next, the particle size distribution (Dv/Dn) of the colored resin particles was calculated.

3. Production of Yellow Toner

The colored resin particles (1) to (9) were covered with external additives to produce yellow toners of Examples 1 to 3 and Comparative Examples 1 to 6.

Example 1

First, 0.6 part of hydrophobized silica fine particles having an average particle diameter of 7 nm and 1 part of hydrophobized silica fine particles having an average particle diameter of 35 nm, were added to 100 parts of the colored resin particles (1). They were mixed by means of a high-speed stirrer (product name: FM Mixer, manufactured by: Nippon Coke & Engineering Co., Ltd.) to prepare the yellow toner of Example 1.

Examples 2 and 3 and Comparative Examples 1 to 6

The yellow toners of Examples 2 and 3 and Comparative Examples 1 to 6 were obtained in the same manner as Example 1, except that the colored resin particles (1) were changed to, as shown in the following Table 1, any of the colored resin particles (2) to (9).

4. Evaluation of Toners for Developing Electrostatic Images

The image density, luminance (L*), color coordinate (a*, b*) and chroma (C*) of the yellow toners of Examples 1 to 3 and Comparative Examples 1 to 6, were measured.

A commercially-available, non-magnetic one-component development color printer (printing rate: 20 sheets/min) was used. The toner cartridge of the development device was filled with a sample yellow toner, and printing sheets were loaded in the printer. Then, the printer was left to stand under an (N/N) environment at a temperature of 23° C. and a relative humidity of 50% for one day. Then, while the amount of the toner supplied onto the developing roller in solid pattern printing was fixed at 0.3 mg/cm², sheets were continuously printed at an image density of 5% from the beginning of the printing. Solid pattern printing (image density: 100%) was carried out on the tenth sheet. Using a McBeth transmitting image densitometer, the image density, luminance (L*), color coordinate (a*, b*) and chroma (C*) of the tenth sheet were measured.

Table 1 shows the measurement and evaluation results of the yellow toners of Examples 1 to 3 and Comparative Examples 1 to 6, along with the toner composition.

In the following Table 1, "PY214" means C.I. Pigment Yellow 214; "PY74" means C.I. Pigment Yellow 74; "PY93" means C.I. Pigment Yellow 93; "PY138" means C.I. Pigment Yellow 138; and "PY155" means C.I. Pigment Yellow 155.

TABLE 1

A

| | Example 1 | Example 2 | Example 3 |
|---|---|---|---|
| Colored resin particles | Particles (1) | Particles (2) | Particles (3) |
| Compound A | PY214 | PY214 | PY214 |
| Surface treatment | Surface-treated | Surface-treated | Surface-treated |
| Added amount (parts) | 3.0 | 4.0 | 6.0 |
| Compound B | PY74 | PY74 | PY74 |
| Surface treatment | Surface-treated | Surface-treated | Surface-treated |
| Added amount (parts) | 5.0 | 5.0 | 4.0 |
| Other yellow colorant | — | — | — |
| Surface treatment | — | — | — |
| Added amount (parts) | — | — | — |
| Compound A/B ratio | 0.6 | 0.8 | 1.5 |
| Dv (μm) | 6.4 | 6.7 | 6.8 |
| Dv/Dn | 1.18 | 1.16 | 1.19 |
| Printing evaluation | | | |
| Amount of toner loaded on sheet (mg/cm²) | 0.3 | 0.3 | 0.3 |
| Reflection density | 1.20 | 1.21 | 1.27 |
| Luminance L* | 94.5 | 95.0 | 95.1 |
| a* | −8.1 | −9.1 | −9.8 |
| b* | 88.6 | 89.3 | 90.0 |
| Chroma C* | 89.3 | 89.7 | 90.5 |
| Hue angle (°) | 95.3 | 95.9 | 96.3 |

B

| | Comparative Example 1 | Comparative Example 2 | Comparative Example 3 |
|---|---|---|---|
| Colored resin particles | Particles (4) | Particles (5) | Particles (6) |
| Compound A | — | — | — |
| Surface treatment | — | — | — |
| Added amount (parts) | — | — | — |
| Compound B | PY74 | PY74 | PY74 |
| Surface treatment | Surface-treated | Surface-treated | Surface-treated |
| Added amount (parts) | 5.0 | 5.0 | 5.0 |
| Other yellow colorant | PY93 | PY138 | PY155 |
| Surface treatment | Surface-treated | Surface-treated | Surface-treated |
| Added amount (parts) | 3.0 | 3.0 | 3.0 |
| Compound A/B ratio | — | — | — |
| Dv (μm) | 6.0 | 6.1 | 6.2 |
| Dv/Dn | 1.23 | 1.18 | 1.19 |
| Printing evaluation | | | |
| Amount of toner loaded on sheet (mg/cm²) | 0.3 | 0.3 | 0.3 |
| Reflection density | 1.14 | 1.10 | 1.17 |
| Luminance L* | 93.0 | 94.2 | 93.1 |
| a* | −7.5 | −8.0 | −7.5 |
| b* | 86.7 | 86.8 | 86.8 |
| Chrome C* | 87.0 | 87.1 | 87.1 |
| Hue angle (°) | 95.0 | 95.3 | 95.0 |

C

| | Comparative Example 4 | Comparative Example 5 | Comparative Example 6 |
|---|---|---|---|
| Colored resin particles | Particles (7) | Particles (8) | Particles (9) |
| Compound A | PY214 | PY214 | — |
| Surface treatment | Surface-treated | Surface-treated | — |
| Added amount (parts) | 8.0 | 10.0 | — |
| Compound B | — | PY74 | PY74 |
| Surface treatment | — | Surface-treated | Surface-treated |
| Added amount (parts) | — | 2.0 | 8.0 |
| Other yellow colorant | — | — | — |
| Surface treatment | — | — | — |

TABLE 1-continued

| | | | |
|---|---|---|---|
| Added amount (parts) | — | — | — |
| Compound A/B ratio | — | 5.0 | — |
| Dv (μm) | 12.9 | 8.8 | 7.0 |
| Dv/Dn | 1.37 | 1.30 | 1.25 |
| Printing evaluation | | | |
| Amount of toner loaded on sheet (mg/cm$^2$) | 0.3 | 0.3 | 0.3 |
| Reflection density | 1.05 | 1.22 | 1.08 |
| Luminance L* | 95.4 | 95.0 | 99.3 |
| a* | −10.9 | −11.0 | −7.1 |
| b* | 69.7 | 83.6 | 89.6 |
| Chroma C* | 70.5 | 84.3 | 89.9 |
| Hue angle (°) | 98.9 | 97.5 | 94.6 |

5. Evaluation of Toners

The yellow toner of Comparative Example 1 is a toner using the compound B (C.I. Pigment Yellow 74) in combination with C.I. Pigment Yellow 93. For Comparative Example 1, the luminance L* is as low as 93.0; the reflection density is as low as 1.14; and the chroma C* is as low as 87.0. Therefore, it is clear that the yellow toner is low in reflection density, dark in color, and dull in color when C.I. Pigment Yellow 93 is used in place of the compound A and the toner on the sheet is 0.3 mg/cm$^2$ and smaller than ever before.

The yellow toner of Comparative Example 2 is a toner using the compound B (C.I. Pigment Yellow 74) in combination with C.I. Pigment Yellow 138. For Comparative Example 2, the luminance L* is as low as 94.2; the reflection density is as low as 1.10; and the chroma C* is as low as 87.1. Therefore, it is clear that the yellow toner is low in reflection density, dark in color, and dull in color when C.I. Pigment Yellow 138 is used in place of the compound A and the toner on the sheet is 0.3 mg/cm$^2$ and smaller than ever before.

The yellow toner of Comparative Example 3 is a toner using the compound B (C.I. Pigment Yellow 74) in combination with C.I. Pigment Yellow 155. For Comparative Example 3, the luminance L* is as low as 93.1; the reflection density is as low as 1.17; and the chroma C* is as low as 87.1. Therefore, it is clear that the yellow toner is low in reflection density, dark in color, and dull in color when C.I. Pigment Yellow 155 is used in place of the compound A and the toner on the sheet is 0.3 mg/cm$^2$ and smaller than ever before.

The yellow toner of Comparative Example 4 is a toner in which, with respect to 100 parts by mass of the binder resin, 8.0 parts by mass of the compound A is only used as the yellow colorant. For Comparative Example 4, the volume average particle diameter (Dv) is as large as 12.9 μm, and the particle size distribution (Dv/Dn) is 1.37. Accordingly, the yellow toner of Comparative Example 4 is a toner with a wide particle size distribution. From these results, it is clear that when the added amount of the compound A is more than 7.5 parts, the particle diameter of the toner thus obtained increases overall, and the toner particles are non-uniform in particle diameter.

For Comparative Example 4, the luminance L* is 95.4. Therefore, there is no problem with luminance. However, for Comparative Example 4, the reflection density is as low as 1.05, and the chroma C* is as low as 70.5. These values are the smallest among the evaluated toners. Therefore, it is clear that the yellow toner is especially low in reflection density and especially dull in color when the compound A is used solely as the yellow colorant and the toner on the sheet is 0.3 mg/cm$^2$ and smaller than ever before.

The yellow toner of Comparative Example 5 is a toner in which, with respect to 100 parts by mass of the binder resin, 10.0 parts by mass of the compound A and 2.0 parts by mass of the compound B were used as the yellow colorant. For Comparative Example 5, the volume average particle diameter (Dv) is as large as 8.8 μm, and the particle size distribution (Dv/Dn) is 1.30. Accordingly, the yellow toner of Comparative Example 5 is a toner with a wide particle size distribution. From these results, it is clear that when the added amount of the compound A is more than 7.5 parts, the particle diameter of the toner thus obtained increases overall, and the toner particles are non-uniform in particle diameter.

For Comparative Example 5, the luminance L* is 95.0, and the reflection density is 1.22. Therefore, there is no problem with luminance and reflection density. For Comparative Example 5, however, the chroma C* is as low as 84.3. Therefore, it is clear that the yellow toner is dull in color when, with respect to 100 parts by mass of the binder resin, the amount of the compound A is larger than 7.5 parts by mass and the amount of the compound B is smaller than 2.5 parts by mass, the compounds being used as the yellow colorant, and the toner on the sheet is 0.3 mg/cm$^2$ and smaller than ever before.

The yellow toner of Comparative Example 6 is a toner in which, with respect to 100 parts by mass of the binder resin, 8.0 parts by mass of the compound B is only used as the yellow colorant. For Comparative Example 6, the volume average particle diameter (Dv) is as large as 7.0 μm, and the particle size distribution (Dv/Dn) is 1.25. Accordingly, the yellow toner of Comparative Example 6 is a toner with a wide particle size distribution. From these results, it is clear that when the compound A is not used, the particle diameter of the toner thus obtained increases overall, and the toner particles are non-uniform in particle diameter.

For Comparative Example 6, the luminance L* is 99.3, and the chroma C* is 89.9. Therefore, there is no problem with luminance and sharpness. For Comparative Example 6, however, the reflection density is as low as 1.08. Therefore, it is clear that the yellow toner is low in reflection density when the compound B is used solely as the yellow colorant and the toner on the sheet is 0.3 mg/cm$^2$ and smaller than ever before.

Meanwhile, the yellow toners of Examples 1 to 3 are toners in which, with respect to 100 parts by mass of the binder resin, 3.0 to 6.0 parts by mass of the compound A and 4.0 to 5.0 parts by mass of the compound B are contained as the yellow colorant. For Examples 1 to 3, the volume average particle diameter (Dv) is as small as 6.4 to 6.8 μm, and the particle size distribution (Dv/Dn) as narrow as 1.16 to 1.19. Therefore, it is clear that the toners of Examples 1 to 3 have the desired average particle diameter and are narrow in particle size distribution.

Also for Examples 1 to 3, the luminance L* is as high as 94.5 or more; the reflection density is as high as 1.20 or more; and the chroma C* is as high as 89.3 or more. Therefore, it is clear that even when the toner on the sheet is 0.3 mg/cm$^2$ and smaller than ever before, the yellow toners of Examples 1 to 3 in which, with respect to 100 parts by mass of the binder resin, 0.5 to 7.5 parts by mass of the compound A and 2.5 to 9.0 parts by mass of the compound B are contained as the yellow colorant, are toners that are better in luminance, reflection density and chroma than ever before.

The invention claimed is:

1. A yellow toner comprising a binder resin and a yellow colorant,
wherein, as the yellow colorant, a compound A represented by the following general formula (1) and a compound B represented by the following formula (2) are contained, and
wherein, with respect to 100 parts by mass of the binder resin, a content of the compound A is from 0.5 to 7.5 parts by mass, and a content of the compound B is from 2.5 to 9.0 parts by mass:

General Formula (1)

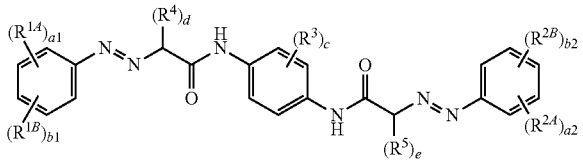

where $R^{1A}$, $R^{1B}$, $R^{2A}$ and $R^{2B}$ are each independently a halogen atom, an alkyl group, a methoxy group, an amino group, a nitro group, an acetylamido group ($-NHCOCH_3$), a methyl ester group ($-COOCH_3$) or a primary amide group ($-CONH_2$);
$R^3$ is a halogen atom;
$R^4$ and $R^5$ are each independently a halogen atom, an alkyl group, a methoxy group, an amino group, a nitro group, an acetylamido group ($-NHCOCH_3$), an acetyl group ($-COCH_3$), a methyl ester group ($-COOCH_3$) or a primary amide group ($-CONH_2$);
a1 and b1 are positive integers that a sum of the positive integers is 1 or more and 3 or less;
a2 and b2 are positive integers that a sum of the positive integers is 1 or more and 3 or less;
c is an integer of 1 or more and 3 or less; and
d and e are each independently 1 or 2, Formula (2)

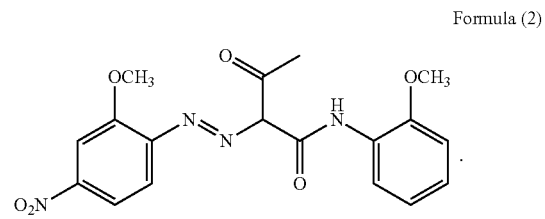 [SMILES: COc1cc([N+](=O)[O-])ccc1/N=N/C(C(C)=O)C(=O)Nc1ccccc1OC]

2. The yellow toner according to claim 1, wherein a mass ratio of the content of the compound A to the content of the compound B (compound A/compound B) is from 0.1 to 2.5.

3. The yellow toner according to claim 1, wherein at least any one of the compound A and the compound B is surface-treated with a coupling agent.

* * * * *